United States Patent
Singh et al.

(10) Patent No.: US 8,575,350 B2
(45) Date of Patent: Nov. 5, 2013

(54) PROCESS FOR PRODUCING PYRIDINE CARBOXYLIC ACIDS

(75) Inventors: Shailendra Kumar Singh, Gajraula (IN); Neeraj Tiwari, Gajraula (IN); Ashutosh Agarwal, Gajraula (IN)

(73) Assignee: Jubilant Life Sciences Ltd, Noida (IN)

( * ) Notice: Subject to any disclaimer, the term of this patent is extended or adjusted under 35 U.S.C. 154(b) by 2 days.

(21) Appl. No.: 13/230,519

(22) Filed: Sep. 12, 2011

(65) Prior Publication Data

US 2012/0065405 A1   Mar. 15, 2012

(30) Foreign Application Priority Data

Sep. 13, 2010   (IN) .......................... 2165/DEL/2010

(51) Int. Cl.
  *C07D 211/78*   (2006.01)
(52) U.S. Cl.
  USPC ........................................................ 546/247
(58) Field of Classification Search
  USPC ....................................................... 546/327
  See application file for complete search history.

(56) References Cited

U.S. PATENT DOCUMENTS

| | | | |
|---|---|---|---|
| 2,494,204 A | 1/1950 | Maxwell et al. | |
| 2,586,555 A | 2/1952 | Mueller | |
| 2,905,688 A | 9/1959 | Illich, Jr. | |
| 3,803,156 A | 4/1974 | Yokoyama et al. | |
| 3,894,971 A * | 7/1975 | Reuter et al. | 502/178 |
| 5,002,641 A | 3/1991 | Toomey, Jr. | |
| 5,728,837 A * | 3/1998 | Alkaeva et al. | 546/320 |
| 6,229,018 B1 | 5/2001 | Heinz et al. | |
| 7,560,566 B2 | 7/2009 | Thomas et al. | |

FOREIGN PATENT DOCUMENTS

| | | |
|---|---|---|
| CN | 1090618 A | 1/1997 |
| EP | 442430 A2 | 8/1991 |
| GB | 757958 A | 9/1956 |
| JP | 07233150 | 9/1995 |
| WO | 9532054 A1 | 11/1995 |

* cited by examiner

*Primary Examiner* — Nizal Chandrakumar
(74) *Attorney, Agent, or Firm* — Maschoff Brennan

(57) ABSTRACT

Disclosed herein cost effective and ecofriendly large scale process for producing pyridine carboxylic acid with high purity and yield at industrial scale.

22 Claims, No Drawings

PROCESS FOR PRODUCING PYRIDINE CARBOXYLIC ACIDS

FIELD OF THE INVENTION

This invention, in general, relates to an improved process for producing pyridine carboxylic acids. More particularly, the present invention provides an improved cost effective and ecofriendly process for large-scale industrial production of pyridine carboxylic acid with high yield and purity.

BACKGROUND OF THE INVENTION

Pyridine carboxylic acids are important intermediate as pharmaceuticals, agrochemicals and food additives. In particular, 3-pyridine carboxylic acid, also called nicotinic acid or niacin is commercially most significant and is used as a precursor of vitamin $B_3$. The 4-pyridine carboxylic acid, also called isonicotinic acid, is used as raw materials for anti-tubercular drugs. It is also regarded as the corrosion inhibitor, electroplate additive, photosensitive resin stabilizer and non-ferrous metals floating agent. The 2-pyridine carboxylic acid is used as anti-acne agent and intermediate for several drugs.

Several processes are reported in the prior art for the production of pyridine carboxylic acids. The known processes differ from each other with respect to the different chemical processes followed.

The processes for the preparation of 3-pyridine carboxylic acid also called nicotinic acid are mainly from liquid phase reaction, vapor phase reaction, electrochemical oxidation and also biological oxidation.

U.S. Pat. No. 2,586,555 reported liquid phase direct oxidation using nitric acid and sulphuric acid at temperatures from 75 to 300° C. and with yields up to 77%. U.S. Pat. No. 2,905,688 reported the process using nitric acid under pressure conditions.

GB757958 discloses preparation of nicotinic and isonicotinic acids by oxidation of alkylpyridines with nitric acid in the vapor phase using $B_2O_3$ and $SeO_2$ as catalysts.

Japanese patent No. 07,233,150 discloses the method for producing nicotinic acid by the process involving liquid-phase oxidation of β-picoline. Thus, β-picoline, $Co(OAc)_2 \cdot 4H_2O$, $Mn(OAc)_4 \cdot 4H_2O$ and 47% aq. HBr are added to an autoclave, pressurized to 100 atm with air and allowed to react at 210° C. for 3 h. The autoclave is cooled, depressurized and cooled to 5° C. and the precipitated crystals are filtered, washed with toluene, and dried to give nicotinic acid, wherein a total of 32% β-picoline is converted and 19% nicotinic acid is converted into β-picoline. To the filtrate β-picoline, $Co(OAc)_2 \cdot 4H_2O$, $Mn(OAc)_4 \cdot 4H_2O$ and 47% aq. HBr are added and resulting mixture is added to the autoclave and pressurized to 100 atm with air, allowed to react at 210° C. for 3 h, and processed to give nicotinic acid with 34% β-picoline conversion ratio and 20.8% conversion of β-picoline into nicotinic acid.

U.S. Pat. No. 7,560,566 reported a process for the production of nicotinic acid which involves contacting 3-methylpyridine with hydrogen peroxide, in the presence of catalyst manganese bromide, in the presence of water as solvent under supercritical conditions close to the supercritical point. The results show good selectivity for nicotinic acid of around 95% at a conversion of about 30%. 3-Pyridine carboxaldehyde is detected with a yield of 1-2%.

Chinese Patent No. CN1090618 discloses bromide-free pyridine carboxylic acids preparation by liquid phase oxidation. 3-Methylpyridine is autoclaved with cobalt acetate, manganese acetate, hydrogen bromide, and aq. acetic acid at 210° C. with supplying air, and then the reaction mixture was hydrogenated over Pd/C at 130° C. and 6 kg/cm² hydrogen for 2 h to give nicotinic acid containing 17 ppm bromine.

Disadvantages of these processes are the high salt production, as well as the production of large streams of waste water. The yield and selectivity's of these processes are quite low and lots of by-products are formed. In some of the processes involving bromides, further purification for removing bromine is required which makes the process complicated and increasing the process steps thereby increasing manufacturing cost. Also, because of high temperature and pressure conditions and multi step processing the processes reported in the prior art are capital intensive.

U.S. Pat. No. 5,002,641 reported the electrochemical synthesis of niacin and other N-heterocyclic compounds. An electrolyte medium is prepared containing 85 parts water by weight, 10 parts α-picoline, and 5 parts picolinic acid. The solution is charged into an undivided cell and electrolyzed using an anodized tin anode with a platinum cathode at a constant current between 0.1 and 1.0 A (10-100 $mAcm^{-2}$). Analysis of the electrolyte indicated an increase in picolinic acid corresponding to 83% current efficiency. The process is also used for the oxidation of quinoline and other methyl pyridine compounds.

European Patent No. 442430 discloses a microbiological process for oxidizing β-picoline to nicotinic acid with a yield of 50% after a reaction time of 16 hours. The unsatisfactory space-time yield and the costly separation of the biomass from the nicotinic acid make industrial application of this process disadvantageous.

The vapor phase oxidation can be done either by ammoxidation of 3-picoline to 3-cyanopyridine followed by liquid phase hydrolysis of 3-cyanopyridine to niacin or directly by the oxidation of 2-methyl-5-ethylpyridine.

Mikhalovskaya et at in Izvestiya Natsional'noi Akademii Nauk Respubliki Kazakhstan, Seriya Khimicheskaya, 2003, 2, 75 have reported oxidation of 4-methylpyridine to isonicotinic acid on Va-Ti—Zr oxide catalyst. 4-Pyridine aldehyde was formed as intermediate oxidation product which on hydrolysis gave isonicotinic acid product.

The vapor phase oxidation of 4-picoline using different catalysts in fluidized bed has been reported. Yang et at in Gaoxiao Huaxue Gongcheng Xuebao, 2007, 448 have reported preparation of isonicotinic acid by vapor-phase oxidation of 4-picoline over V—Ti—Cr—Al—P oxide catalyst prepared by an impregnation method. Under optimum conditions, the product yield reached 82%.

Afanas'eva et al in Khimiya Geterotsiklicheskikh Soedinenii, 1968, 1, 142 have reported the preparation of isonicotinic acid by vapour phase catalytic oxidation of trimethylol-4-picoline. The process involves reacting 1 mole of trimethylol-4-picoline, 150-200 moles $H_2O_2$ and 125-200 moles oxygen for 0.35-0.45 sec. contact time on a tin vanadate catalyst in a 280 mm quartz-tube, 20 mm in diameter to give isonicotinic acid in 65% yield.

In the recent past, there are literature references which reported vapor phase oxidation of β-picoline using vanadia based catalyst.

U.S. Pat. No. 3,803,156 provides a process for producing pyridine carboxylic acid, which comprises contacting methylpyridine, molecular oxygen-containing gas, and water with solid oxidation catalyst containing a vanadium compound bonded with oxygen in the vapor phase to produce pyridine carboxylic acid. In this process, minor amount of oxides of germanium, tin, indium, niobium, tantalum, gallium, and zirconium are used as promoter. This process has disadvantages of high reaction temperature and a large amount of water which in turn increases the energy consumption during purification.

U.S. Pat. No. 5,728,837 discloses the process for preparing nicotinic acid with a yield of 82-86%. The disclosed process involves gas phase oxidation of β-picoline with oxygen in the presence of water vapor over vanadia based catalyst at a temperature of 250-290° C. and mole ratio of oxygen:β-picoline 15-40:1 and water:β-picoline 10-70:1. Further, the nicotinic acid is isolated by crystallization in a tube crystallizer at a temperature of 160-200° C.

European Patent No. 762933 also discloses a process for the preparation of a highly selective catalyst for the ammoxidation of alkylpyridines to cyanopyridines which on further hydrolysis give pyridine carboxylic acid. The catalyst composition disclosed is $V_aTi_bZr_cO_x$, wherein a is 1, b is 7.5-8, c is 0.5, x represents the number of oxygen atoms.

U.S. Pat. No. 2,494,204 discloses the process for the preparation of picolinic acid. The process involves reacting equimolar amounts of cyanogen and butadiene in the vapor phase at 480° C., contact time of 87 seconds to give 18.1% of 2-cyanopyridine which is converted to picolinic acid.

U.S. Pat. No. 6,229,018 reported the preparation of nicotinic acid by the direct oxidation of β-picoline in the gas phase, wherein water and β-picoline are fed separately into the catalyst. The catalyst, vanadium oxide is supported on titanium oxide which is produced by sulfuric acid method and the support titanium oxide has high specific surface area. It has been disclosed that when the specific surface area of the titanium dioxide support is greater than 250 m$^2$/g, and the amount of vanadium oxide content is at least 20% by weight, the yields are high. However, if the titanium oxide having low specific surface area and vanadium oxide in low amount is used for the oxidation process, the yield of the nicotinic acid is reduced. Carbon dioxide produced in the process is partially recycled back in the reactor to bring about an additional improvement in the nicotinic acid yield. The recovery of niacin, involves desublimation process at 235° C. by installing a tubular crystallizer at the reactor outlet. German Patent No. 19822788 discloses the oxidation of 5-ethyl-2-methylpyridine with vanadium oxide based catalyst, supported on $Al_2O_3$ and/or $ZrO_2$ with specific surface 1-50 m$^2$/g. The process involves passing 5-ethyl-2-methylpyridine (2 mg/min), air (80 mL/min), and $H_2O$ (0.2 g/min) over 10 g of $LiV_6O_{15}$/$ZrSiO_4$ catalyst at 320° C. for 900 min to give 100% conversion and a 66% yield of nicotinic acid.

The direct catalytic vapor phase oxidation of alkyl pyridines has lot of advantages over other processes. The vapor phase process uses air as oxidant instead of stoichiometric large excess of chemical oxidizing agents. The reaction is carried out at atmospheric pressure. The only solvent used is water. The process is highly selective therefore waste generation is very less. Another advantage is that there are very few unit operations necessary to obtain the pure product.

However, most of the processes reported in the prior art are carried out at very small scale in laboratory. As oxidation of alkyl pyridine with oxygen is a highly exothermic reaction, under the given process conditions at larger scale, there is generation of hot spots, on the top of the catalyst bed at feed introduction point because of higher concentration of alkyl pyridine at initial stage. This results in runaway conditions of the reaction temperature, and therefore not very safe to operate at large scale. Also the non uniform temperature profile across the catalyst bed affects selectivity as well as quality of the product.

Also, the recovery from the reaction mass has been reported by following desublimation process, incorporating crystallizer. Design of a suitable crystallizer for large volume is very challenging and is not commercially proven.

There are also many other literature references which proposes alternate methods with or without use of organic solvents for recovery and purification of pyridine carboxylic acids from the reaction mass but none of the prior art processes can be practiced at large scale because of many disadvantages associated with the process to be feasible for large scale production. Hence, these processes can only be operated at laboratory scale and are not suitable at larger scale.

Moreover, the processes disclosed in the prior art include multiple steps for extraction and isolation to obtain the desired products. The prior art processes involves time-consuming purification process at each step, which results in wasteful material, consequently making the process costly and uneconomical. Further, the processes can be used for producing small batches of the desired products in low yield and at higher costs, hence making the processes unsuitable for large-scale production.

In view of the increasing demand for producing pyridine carboxylic acid of high purity and yield, it is therefore desirable to develop a commercially and economically viable process for large scale industrial manufacturing of pyridine carboxylic acid with high purity and yield which can address the above mentioned problems associated with the known processes. Further, the process should be temperature controlled and involve use of fewer purification steps.

SUMMARY OF THE INVENTION

It is an embodiment of the present invention to provide a process for producing pyridine carboxylic acid, wherein the process enables production of highly pure pyridine carboxylic acid compounds at industrial scale with minimum generation of effluents.

It is another embodiment of the present invention to provide a cost effective and commercially viable process for producing pyridine carboxylic acid wherein the process provides highly pure product, simplifying isolation steps by avoiding multi stage operation.

It is another embodiment of the present invention to provide a cost effective and commercially viable process for producing pyridine carboxylic acid wherein the process comprises recovering and effectively recycling of raw materials and solvents.

The above and other embodiments of the present invention are further attained and supported by the following embodiments described herein. However, the scope of the invention is not restricted to the described embodiments herein after.

In accordance with one embodiment of the present invention, there is provided an industrial process for producing pyridine carboxylic acid from corresponding alkyl pyridine, wherein the process comprises oxidizing alkyl pyridine with oxygen or a source of oxygen in presence of water and a vanadia based catalyst along with catalyst support and metalloid additive, wherein multi layered packing of said catalyst is employed and isolating the pyridine carboxylic acid.

In accordance with another embodiment of the present invention, there is provided an industrial process for producing pyridine carboxylic acid from corresponding alkyl pyridine, wherein the catalyst used is oxide of vanadium along with oxide of titanium as a support and oxide of metalloid additive.

In accordance with one other embodiment of the present invention, there is provided an industrial process for producing pyridine carboxylic acid from corresponding alkyl pyridine, wherein the oxide of vanadium to oxide of titanium to oxide of metalloid additive is having a mole ratio of 1:5-15: 0.1-0.5.

In accordance with still another embodiment of the present invention, there is provided an industrial process for producing pyridine carboxylic acid, wherein the pyridine carboxylic acid is isolated by scrubbing or extraction.

In accordance with yet another embodiment of the present invention, there is provided an industrial process for isolating pyridine carboxylic acid, wherein the process comprises preparing pyridine carboxylic acid by oxidizing alkyl pyridine with oxygen or source of oxygen in presence of water, scrubbing the resultant product gases in primary absorber, optionally scrubbing the unscrubbed gases in secondary absorber, desirably treating the resultant pyridine carboxylic acid solution with activated carbon, filtering the resultant mass, optionally crystallizing the resultant mass and drying the same to obtain pyridine carboxylic acid.

In accordance with yet another embodiment of the present invention there is provided an industrial process for producing pyridine carboxylic acid, wherein the isolation is performed in the temperature range of 5-120° C. under atmospheric or super atmospheric or low pressure condition.

In accordance with yet another embodiment of the present invention there is provided an industrial process for producing pyridine carboxylic acid, wherein the unreacted alkyl pyridine compound, by products and effluents generated are recoverable and effectively recyclable.

Other aspects will be set forth in the description which follows, and in part will be apparent from the description or may be learnt by the practice of the invention.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

This invention, in general, relates to an improved process for producing pyridine carboxylic acids. More particularly, the present invention provides an improved cost effective and ecofriendly process for large-scale industrial production of pyridine carboxylic acid with high yield and purity.

The disclosed embodiment of the present invention deals with an industrial process for producing pyridine carboxylic acid. The process of the present invention is advantageous as it involves better carbon efficiency and minimum effluent load. In addition, the process eliminates undesired processing steps thereby making the process commercially viable and feasible for large-scale manufacture of pure pyridine carboxylic acid. Also, because of mild temperature and pressure conditions and few processing steps, the disclosed process of the present invention is safer and less capital intensive.

The disclosed embodiment of the present invention deals with a process for the large scale production of pyridine carboxylic acid that has advantages over prior art processes. The process is suitable and can be practiced at large scale. If the processes reported in the prior art are performed under the reported process conditions at larger scale, there is the generation of hot spots, with high temperature gradient across catalyst bed. This results in runaway conditions of the reaction temperature, and therefore are not safe to operate at large scale. Also the random temperature profile across the catalyst bed affects selectivity as well as quality of pyridine carboxylic acid.

According to the preferred embodiment of the present invention there is provided an improved industrial process for the production of pyridine carboxylic acid with high purity and yield.

According to the present invention the process for producing pyridine carboxylic acid comprises oxidizing alkyl pyridine with oxygen or a source of oxygen in presence of water and a vanadia based catalyst along with catalyst support and metalloid additive, wherein multi layered packing of said catalyst is employed and isolating the pyridine carboxylic acid.

According to the present invention, the metalloid additive used in the process is selected from the group comprising of boron, silicon, germanium, arsenic, antimony, tellurium, polonium and mixtures thereof.

According to one of the preferred embodiments of the present invention, the process employs multi layered packing of the catalyst to achieve uniform temperature profile across the catalyst bed, thus making the process suitable for large scale production, wherein the packing of the catalyst bed is done with a compound selected from the group comprising of silica, alumina, silicon carbide, titanium oxide, diatomaceous earth, zeolite or mixture thereof, preferably inert alumina.

According to the present invention, the alkyl pyridine compound used according to the present invention includes a compound of the formula:

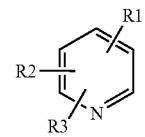

wherein $R_1$, $R_2$ and $R_3$ are the same or different and each independently a hydrogen atom or a lower alkyl group having 1 to 4 carbon atoms with the proviso that at least one of them is the alkyl group. Specific examples of the alkyl-substituted heteroaromatic compound are 2-methylpyridine; 3-methylpyridine; 4-methylpyridine; 2,3-dimethylpyridine; 2,4-dimethylpyridine; 2,5-dimethylpyridine; 2,6-dimethylpyridine; 3,4-dimethylpyridine; 3,5-dimethylpyridine; 2-methyl-5-ethylpyridine; 2,4,6-trimethylpyridine; 2,3,4-trimethylpyridine; 2,3,5-trimethylpyridine; 2,3,6-trimethylpyridine.

According to the present invention, the alkyl pyridine used in the process is β-picoline and the pyridine carboxylic acid obtained is nicotinic acid.

According to the present invention, the alkyl pyridine used in the process is γ-picoline and the pyridine carboxylic acid obtained is isonicotinic acid.

According to the present invention, the alkyl pyridine used in the process is α-picoline and the pyridine carboxylic acid obtained is picolinic acid.

According to the present invention the catalyst used is an oxide of vanadium with oxide of titanium as support and oxide of metalloid additive in a mole ratio 1:5-15:0.1-0.5.

According to the present invention, the composition of catalyst used in the process is $x(V_2O_5)$-$y(TiO_2)$-$z(M_aO_b)$, where x=5-40% by weight, y=95-60% by weight, z=1-10% by weight and M is metalloid additive.

The oxidation reaction is carried out in the temperature range of about 240 to 380° C., preferably about 250 to 290° C.

The reactor is selected from fixed bed, fluidized bed and moving bed reactor.

According to the present invention, alkylpyridine, water and air are vaporized and fed from the top of a reactor, which is packed with catalyst. The mole ratio of oxygen:alkyl pyridine is in the range of 10-40:1; preferably 15-30:1.

The mole ratio of water:alkylpyridine is in the range of 20-80:1; preferably 30-60:1. The oxidation is carried out at a weight hour space velocity (WHSV) of 0.01 to 2.0 $hr^{-1}$; preferably from 0.02 to 0.75 $hr^{-1}$.

According to the present invention, the catalyst support has a specific surface area greater than 100 $m^2/g$; preferably in the range 100-300 $m^2/g$.

According to the present invention, the catalyst has a specific surface area in the range 20-50 $m^2/g$.

According to one of the preferred embodiments of the present invention, the pyridine carboxylic acid is isolated by scrubbing or by extraction. The scrubbing or extraction is carried out with solvent selected from water, methanol, ethanol, n-propanol, isopropanol, n-butanol, acetone, pyridine, tetrahydrofuran, furfuryl alcohol, tetrahydrofurfuryl alcohol, acetic acid, formic acid and mixtures thereof.

According to the present invention, there is provided an isolation of pyridine carboxylic acid, wherein said isolation process comprises preparing pyridine carboxylic acid by oxidizing alkyl pyridine with oxygen or source of oxygen in presence of water to obtain product gases, scrubbing the resultant product gases in primary absorber, optionally scrubbing the unscrubbed gases in a secondary absorber, desirably treating resultant pyridine carboxylic acid solution with activated carbon, filtering the resultant mass, optionally crystallizing the resultant mass, and drying the filtered mass or crystallized mass to obtain pyridine carboxylic acid.

During the isolation step, product gases from the reactor are directly scrubbed with suitable solvent in a primary absorber. Majority of pyridine carboxylic acid is absorbed in circulating liquid. Unscrubbed gases, if present, are scrubbed in secondary absorber. In secondary absorber, un-reacted alkyl pyridine, other organic by products and flue gases are absorbed in solvent which is recycled back to reactor. Scrubbed solution of primary absorber is desirably treated with activated carbon to remove coloring impurities. After carbon treatment, the mass is filtered in hot conditions, crystallized, and the wet cake obtained is dried to get pyridine carboxylic acid, meeting desired product specifications.

According to the process of the present invention, the isolation is performed in the temperature range of 5-120° C. under atmospheric or super atmospheric or low pressure condition.

The scrubbing in primary absorber is performed in the temperature range of 5-120° C. under atmospheric or super atmospheric or low pressure condition.

According to the process of the present invention, the pyridine carboxylic acid obtained is dried at a temperature of from about 80-120° C.

According to one of the preferred embodiments of the present invention, flue gases from the absorbers, scrubbed liquid and mother liquor are recycled back.

The present invention is further illustrated below with reference to the following examples without intending to limit the scope of the invention in any manner.

EXAMPLE 1

A 5 liter, 4 necked round bottomed flask fitted with agitator was charged with water. The oxalic acid was added with continuous stirring at 60-80° C. To this solution vanadium pentoxide and antimony trioxide ($Sb_2O_3$) were slowly added followed with titanium dioxide ($TiO_2$). The reaction mass was maintained for 2 hrs at 60-80° C. and then evaporated to get it in a suitable paste for extrusion/pelletization/spray drying.

EXAMPLE 2

The catalyst was prepared by following the method as described in Example 1 except that antimony trioxide was not added.

EXAMPLE 3

The catalyst was prepared by following the method described in Example 1 except at pilot scale. 55 kg of catalyst was prepared by using 500 lit S.S reactor, pilot scale sigma mixer, extruder and calcinator for pilot plant study.

EXAMPLE 4

500 gm of catalyst, prepared as per Example 1 was placed in a S.S 316 tubular reactor equipped with heating and cooling arrangement. The catalyst bed was heated in the presence of air/nitrogen to 260° C. The reaction temperature was maintained to 260-280° C. β-Picoline and air were fed separately through vaporizers. The mole feed ratio of oxygen:water:β-Picoline was 25:40:1 and WHSV was 0.05 $hr^{-1}$. The product gases from reactor were scrubbed with water in primary absorber at 70-80° C. The unscrubbed gases from primary absorber were scrubbed in secondary absorber at ambient temperature. In secondary absorber, un-reacted β-picoline and other organics were absorbed in water and recycled back to reactor along with vent gases with optimum purge and accordingly necessary make up. The solution from absorber was treated with activated carbon to remove coloring impurities and the obtained mass was filtered, crystallized and dried to obtain light reddish colored nicotinic acid (assay 98.2%) with selectivity of 82.5% and 91.7% conversion of β-picoline.

EXAMPLE 5

The nicotinic acid was prepared by the process as described in Example 4 using the catalyst prepared in Example 1. The catalyst was packed in the reactor in four layers maintaining 25-100% catalyst by mixing with inert alumina balls.

White color nicotinic acid with assay 99.76% was isolated with 89.5% conversion of β-picoline and selectivity of 94.6%.

EXAMPLE 6

The nicotinic acid was prepared by the process as described in Example 4, except using the catalyst prepared in Example 2. The product obtained was light brown with 78.0% selectivity of nicotinic acid and 97% conversion of β-picoline.

EXAMPLE 7

The isonicotinic acid was prepared by the process as described in Example 5 except that the temperature was maintained at 320-340° C. The catalyst prepared in Example 1 was used.

White to off white color isonicotinic acid with assay 99.2% was isolated with 88% conversion of γ-picoline and selectivity of 80%.

EXAMPLE 8

The catalyst was prepared by the method as described in Example 3 and process conditions were maintained as per Example 5 except that the process was carried out at large scale. The catalyst was packed as per Example 5 in a tubular reactor. Total volume of the reactor was 75 liters and equipped with heating and cooling arrangement. The catalyst bed was heated in the presence of air/nitrogen to 250° C. β-picoline, water and air were fed separately through a vaporizer from top of the reactor. The molar feed ratio of oxygen:water:β-picoline was 20:40:1 and WHSV was 0.05 hr$^{-1}$. The nicotinic acid was isolated by the method as described in Example 4. The vent gases and scrubbed liquid obtained from secondary absorber and mother liquor of first absorber was recycled back in the process with optimum purge. The nicotinic acid obtained was white colored. Selectivity: 90.8%; β-picoline conversion of 94.6%. Assay: 99.58%.

While this invention has been described in detail with reference to certain preferred embodiments, it should be appreciated that the present invention is not limited to those precise embodiments rather, in view of the present disclosure, which describes the current best mode for practicing the invention, many modifications and variations, would present themselves to those skilled in the art without departing from the scope and spirit of this invention. This invention is susceptible to considerable variation in its practice within the spirit and scope of the appended claims.

We claim:

1. A process for preparing pyridine carboxylic acid, the process comprising:
   oxidizing alkyl pyridine with oxygen and/or air in presence of water and a vanadia based catalyst, and
   isolating the pyridine carboxylic acid,
   wherein the said catalyst comprises pellets of an oxide of vanadium with oxide of titanium as a support and oxide of metalloid as an additive and wherein the said catalyst pellets are packed in a reactor in a multilayer arrangement, wherein the catalyst includes pellets having $x(V_2O_5)$-$y(TiO_2)$-$z(M_aO_b)$, where x=5-40% by weight, y=95-60% by weight, z=1-10% by weight and M is the metalloid additive.

2. The process according to claim 1, wherein the oxide of vanadium to oxide of titanium to oxide of metalloid additive is having a mole ratio of 1:5-15:0.1-0.5.

3. The process according to claim 1, wherein the packing of catalyst bed is done with a compound selected from the group comprising silica, alumina, silicon carbide, titanium oxide, diatomaceous earth, zeolite and mixtures thereof.

4. The process according to claim 1, wherein the packing of catalyst bed is done with inert alumina mixed with the catalyst and arranged in the multilavers, wherein each layer has a different proportion of the catalyst pellets and inert alumina.

5. The process according to claim 1, wherein the metalloid additive is selected from the group comprising boron, silicon, germanium, arsenic, antimony, tellurium, polonium and mixtures thereof.

6. The process according to claim 1, wherein the oxidation is carried out in the temperature range of 240 to 380° C.

7. The process according to claim 1, wherein the mole ratio of oxygen and alkyl pyridine is in the range of 10-40:1.

8. The process according to claim 1, wherein the mole ratio of water: alkyl pyridine is in the range of 20-80:1.

9. The process according to claim 1, wherein the catalyst support has a specific surface area greater than 100m$^2$/g.

10. The process according to claim 1, wherein the catalyst has a specific surface area in the range 20-50 m$^2$/g.

11. The process according to claim 1, wherein the oxidation is carried out at a weight hour space velocity (WHSV) of 0.01 to 2.0 hr$^{-1}$.

12. The process according to claim 1, wherein the amount of vanadium oxide is in the range of 5-40% by weight.

13. The process according to claim 1, wherein the pyridine carboxylic acid is isolated by scrubbing or by extraction.

14. The process according to claim 13, wherein the scrubbing or extraction is carried out with solvent selected from water, methanol, ethanol, n-propanol, isopropanol, n-butanol, acetone, pyridine, tetrahydrofuran, furfuryl alcohol, tetrahydrofurfuryl alcohol, acetic acid, formic acid and mixtures thereof.

15. The process according to claim 1, wherein the isolation is performed in the temperature range of 5-120° C. under atmospheric or super atmospheric or low pressure condition.

16. The process according to claim 1, wherein the alkyl pyridine is β-picoline and the pyridine carboxylic acid is nicotinic acid, wherein the alkyl pyridine is γ-picoline and the pyridine carboxylic acid is isonicotinic acid or wherein the alkyl pyridine is α-picoline and the pyridine carboxylic acid is picolinic acid.

17. The process according to claim 1, the process comprising:
   preparing pyridine carboxylic acid by oxidizing alkyl pyridine with oxygen and/or air in presence of water to obtain product gases;
   scrubbing the resultant product gases in a primary absorber;
   optionally scrubbing unscrubbed gases in a secondary absorber;
   desirably treating a resultant pyridine carboxylic acid solution with activated carbon to obtain a mass;
   filtering the resultant mass;
   optionally crystallizing the resultant mass, and
   drying the filtered mass or crystallized mass to obtain pyridine carboxylic acid.

18. The process according to claim 17, wherein the scrubbing in primary absorber is performed at a temperature range of 5-120° C. under atmospheric or super atmospheric or low pressure condition.

19. The process according to claim 17, wherein the pyridine carboxylic acid is dried at a temperature range of about 80-120° C.

20. The process according to claim 17, wherein flue gases from the absorber, scrubbed liquid and mother liquor obtained in the process are recycled.

21. The process according to claim 17, wherein the alkyl pyridine is β-picoline and the pyridine carboxylic acid is nicotinic acid, wherein the alkyl pyridine is γ-picoline and the pyridine carboxylic acid is isonicotinic acid or wherein the alkyl pyridine is α-picoline and the pyridine carboxylic acid is picolinic acid.

22. The process according to claim 4, wherein the inert alumina and catalyst relative proportion ranges from about 25% to about 100% being the catalyst.

* * * * *